(12) United States Patent
Winquist et al.

(10) Patent No.: US 7,846,189 B2
(45) Date of Patent: *Dec. 7, 2010

(54) ORTHOPAEDIC BONE PLATE

(75) Inventors: Robert A Winquist, Seattle, WA (US); Steve Benirschke, Seattle, WA (US); Paul Duwelius, Lake Oswego, OR (US); Raymond Desjardins, Arnprior (CA); David Templeman, Plymouth, MN (US); John E Meyers, Columbia City, IN (US); Stanley W Patterson, Warsaw, IN (US); Gregory G Price, Warsaw, IN (US); James Goulet, Ann Arbor, MI (US)

(73) Assignee: Zimmer, Inc., Warsaw, IN (US)

( * ) Notice: Subject to any disclaimer, the term of this patent is extended or adjusted under 35 U.S.C. 154(b) by 1623 days.

This patent is subject to a terminal disclaimer.

(21) Appl. No.: 10/738,786

(22) Filed: Dec. 17, 2003

(65) Prior Publication Data
US 2004/0186477 A1 Sep. 23, 2004

Related U.S. Application Data

(63) Continuation of application No. 09/938,071, filed on Aug. 23, 2001, now Pat. No. 6,682,531, which is a continuation of application No. 09/309,368, filed on May 11, 1999, now Pat. No. 6,355,042, which is a continuation of application No. 09/052,539, filed on Mar. 31, 1998, now Pat. No. 5,938,664.

(51) Int. Cl.
*A61B 17/80* (2006.01)
(52) U.S. Cl. ...................... 606/280; 606/284

(58) Field of Classification Search ............ 606/69–71
See application file for complete search history.

(56) References Cited

U.S. PATENT DOCUMENTS 3,668,972 A   6/1972   Allgower et al.

(Continued)

FOREIGN PATENT DOCUMENTS

FR   2405062   5/1979

(Continued)

OTHER PUBLICATIONS

Pure Titanium Implants, SYNTHES®, Dec. 1993.

(Continued)

*Primary Examiner*—Thomas C Barrett
*Assistant Examiner*—Nicholas Woodall
(74) *Attorney, Agent, or Firm*—Baker & Daniels LLP

(57) ABSTRACT

An orthopaedic bone plate is coupled to a bone having an enlarged head at one end thereof which is attached to a shaft. The bone plate includes an elongate portion, a flared portion and an intermediate portion. The elongate portion is attachable to the bone shaft using a plurality of bone screws. The elongate portion generally defines a longitudinal axis. The flared portion is attachable to the bone head using at least one bone screw. The intermediate portion interconnects the elongate portion and the flared portion. The intermediate portion is structured and arranged to allow the elongate portion and the flared portion to move relative to each other in a direction transverse to the longitudinal axis when the elongate portion and the flared portion are attached to the bone.

20 Claims, 2 Drawing Sheets

U.S. PATENT DOCUMENTS

| | | | |
|---|---|---|---|
| 3,748,778 A | | 7/1973 | Ellies et al. |
| 3,882,630 A | | 5/1975 | Bianco |
| 4,219,015 A | | 8/1980 | Steinemann |
| 4,454,876 A | * | 6/1984 | Mears .................. 606/69 |
| RE31,628 E | | 7/1984 | Allgower et al. |
| 4,465,065 A | | 8/1984 | Gotfried |
| 4,488,543 A | | 12/1984 | Tornier |
| 4,493,317 A | | 1/1985 | Klaue |
| 4,503,848 A | | 3/1985 | Caspar |
| 4,513,744 A | | 4/1985 | Klaue |
| 4,565,193 A | | 1/1986 | Streli |
| 4,651,724 A | | 3/1987 | Berentey et al. |
| 4,667,664 A | | 5/1987 | Taylor et al. |
| 4,762,122 A | | 8/1988 | Slocum |
| 4,776,330 A | | 10/1988 | Chapman et al. |
| 4,781,183 A | | 11/1988 | Casey et al. |
| 4,800,874 A | | 1/1989 | David et al. |
| 4,867,144 A | | 9/1989 | Karas et al. |
| 4,955,886 A | | 9/1990 | Pawluk |
| 4,966,599 A | * | 10/1990 | Pollock .................. 606/69 |
| 4,988,350 A | | 1/1991 | Herzberg |
| 5,006,120 A | | 4/1991 | Carter |
| 5,015,248 A | | 5/1991 | Burstein et al. |
| 5,021,056 A | | 6/1991 | Hofmann et al. |
| 5,041,113 A | | 8/1991 | Biedermann et al. |
| 5,041,114 A | | 8/1991 | Chapman et al. |
| 5,053,039 A | | 10/1991 | Hofmann et al. |
| 5,190,545 A | | 3/1993 | Corsi et al. |
| 5,304,180 A | * | 4/1994 | Slocum .................. 606/69 |
| 5,314,431 A | | 5/1994 | Graziano |
| 5,364,398 A | | 11/1994 | Chapman et al. |
| 5,372,598 A | | 12/1994 | Luhr et al. |
| 5,413,577 A | * | 5/1995 | Pollock .................. 606/280 |
| 5,429,641 A | | 7/1995 | Gotfried |
| 5,527,311 A | * | 6/1996 | Procter et al. .......... 606/280 |
| 5,578,038 A | | 11/1996 | Slocum |
| 5,634,926 A | | 6/1997 | Jobe |
| 5,690,631 A | * | 11/1997 | Duncan et al. .......... 606/69 |
| 5,718,704 A | * | 2/1998 | Medoff .................. 606/69 |
| 5,718,705 A | * | 2/1998 | Sammarco .............. 606/284 |
| 5,752,958 A | | 5/1998 | Wellisz |
| 5,766,176 A | * | 6/1998 | Duncan .................. 606/281 |
| 5,779,706 A | * | 7/1998 | Tschakaloff ............ 606/69 |
| 5,785,712 A | | 7/1998 | Runciman et al. |
| 5,827,286 A | | 10/1998 | Incavo et al. |
| 5,855,580 A | | 1/1999 | Kreidler et al. |
| 5,931,839 A | | 8/1999 | Medoff |
| 5,938,662 A | | 8/1999 | Rinner |
| 5,938,664 A | | 8/1999 | Winquist et al. |
| 5,947,970 A | | 9/1999 | Schmelziesen et al. |
| 5,964,763 A | | 10/1999 | Incavo et al. |
| 5,968,047 A | | 10/1999 | Reed |
| 6,077,271 A | * | 6/2000 | Huebner et al. ........ 606/101 |
| 6,096,040 A | | 8/2000 | Esser |
| 6,123,709 A | * | 9/2000 | Jones .................... 606/281 |
| 6,183,475 B1 | | 2/2001 | Lester et al. |
| 6,206,882 B1 | | 3/2001 | Cohen |
| 6,221,073 B1 | | 4/2001 | Weiss et al. |
| D443,060 S | | 5/2001 | Benirschke et al. |
| 6,283,969 B1 | | 9/2001 | Grusin et al. |
| 6,355,042 B2 | | 3/2002 | Winquist et al. |
| 6,358,250 B1 | | 3/2002 | Orbay |
| 6,364,881 B1 | | 4/2002 | Apgar et al. |
| 6,364,882 B1 | | 4/2002 | Orbay |
| D458,374 S | | 6/2002 | Bryant et al. |
| D458,683 S | | 6/2002 | Bryant et al. |
| D458,684 S | | 6/2002 | Bryant et al. |
| D458,996 S | | 6/2002 | Bryant et al. |
| 6,440,135 B2 | | 8/2002 | Orbay et al. |
| D463,557 S | | 9/2002 | Bryant et al. |
| D463,558 S | | 9/2002 | Bryant et al. |
| D463,559 S | | 9/2002 | Bryant et al. |
| D464,136 S | | 10/2002 | Bryant et al. |
| D464,731 S | | 10/2002 | Bryant et al. |
| 6,488,685 B1 | * | 12/2002 | Manderson ............ 606/69 |
| D469,532 S | | 1/2003 | Bryant et al. |
| D469,533 S | | 1/2003 | Bryant et al. |
| D469,534 S | | 1/2003 | Bryant et al. |
| D469,874 S | | 2/2003 | Bryant et al. |
| D469,875 S | | 2/2003 | Bryant et al. |
| D470,588 S | | 2/2003 | Bryant et al. |
| D479,331 S | | 9/2003 | Pike et al. |
| D480,141 S | | 9/2003 | Benirschke et al. |
| 6,623,486 B1 | | 9/2003 | Weaver et al. |
| 6,682,531 B2 | | 1/2004 | Winquist et al. |
| 6,712,820 B2 | | 3/2004 | Orbay |
| 6,796,986 B2 | | 9/2004 | Duffner |
| D520,637 S | | 5/2006 | Kay et al. |
| D536,453 S | | 2/2007 | Young et al. |
| 2002/0156474 A1 | | 10/2002 | Wack et al. |
| 2004/0030339 A1 | | 2/2004 | Wack et al. |
| 2004/0059335 A1 | | 3/2004 | Weaver |
| 2004/0102777 A1 | | 5/2004 | Huebner |
| 2004/0102778 A1 | | 5/2004 | Huebner et al. |
| 2004/0116930 A1 | | 6/2004 | O'Driscoll et al. |
| 2004/0122429 A1 | | 6/2004 | Phillips et al. |
| 2004/0225291 A1 | | 11/2004 | Schwammberger et al. |
| 2004/0260291 A1 | | 12/2004 | Jensen |
| 2005/0010226 A1 | | 1/2005 | Grady, Jr. et al. |
| 2005/0085818 A1 | | 4/2005 | Huebner |
| 2005/0085825 A1 | | 4/2005 | Castaneda |
| 2006/0173458 A1 | | 8/2006 | Forstein et al. |
| 2007/0162015 A1 | | 7/2007 | Winquist et al. |

FOREIGN PATENT DOCUMENTS

| | | |
|---|---|---|
| FR | 2405705 | 5/1979 |
| GB | 2245498 A | 1/1992 |
| GB | 2 245 498 | 12/1996 |

OTHER PUBLICATIONS

Sales Brochure—Pure Titanium Implants, SYNTHES®, Dec. 1993—discloses bone plates that continuously taper proximally over a portion of the length of the bone plate. Applicants have observed what they believe to be a sample of the Titanium LC-DCP® Condylar Buttress Plate disclosed in this document deflecting in response to a force transverse to the shaft being applied to the proximal end of the bone plate while the shaft is held in place.

Article—Holding Power and Reinforcement of Cancellous Screws in Human Bone, Kleeman et al., Clinical Orthopaedics and Related Research, No. 284, Nov. 1992.

Plates, Zimmer Inc., 1987.

Zimmer ECT Internal fracture Fixation Systems, 1987.

Zimmer Periarticular Distal Radial Locking Plates Surgical Technique, Hanel, et al., Copyright 2005—2 parts 10 pages, 11 pages.

Zimmer Periarticular Distal Tibial Locking Plates Surgical Technique, Benirschke et al., Copyright 2005—28 pages.

Zimmer Periarticular Proximal Tibial Locking Plate Surgical Technique, Benirschke et al., Copyright 2005—2 parts 10 pages, 10 pages.

Zimmer Periarticular Distal Femoral Locking Plate Surgical Technique, Benirschke et al., Copyright 2005—20 pages.

Zimmer Periarticular Proximal Humeral Locking Plate Surgical Technique, Benirschke et al., Copyright 2005—21 pages.

Numelock II Polyaxial Locking Ssytem—Operative Technique, Stryker Trauma, Copyright 2004—20 pages.

Philos + Plilos Long. The Anatomic Fixation System for the Proximal Humerus With Angular Stability—Surgical Technique, Synthes, Copyright 2005—1 page.

Large Fragment Locking Compression Plate (LCP)—Technique Guide, Synthes, Copyright 2003—23 pages.

Muller et al., Techniques Recommended by the OA-ASIF Group (1991), pp. 204-217 and 568-574.

* cited by examiner

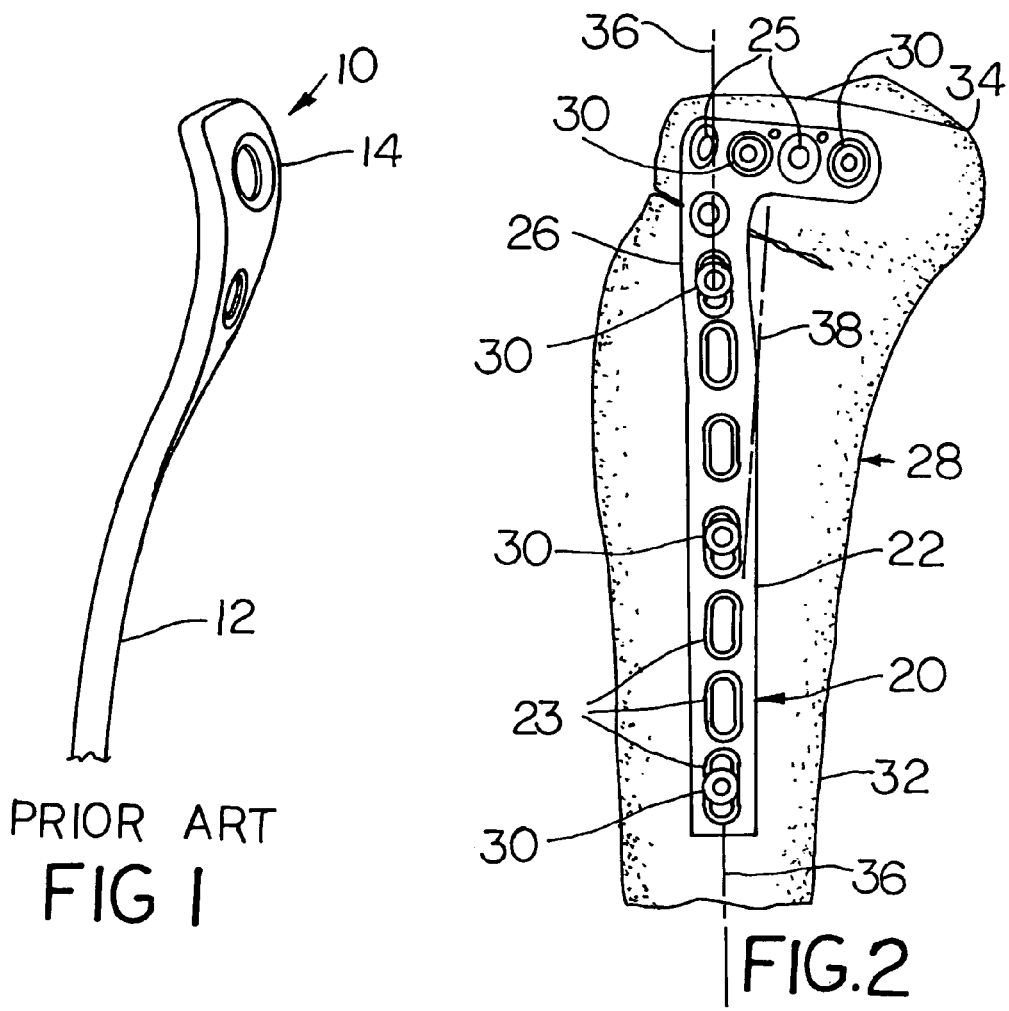
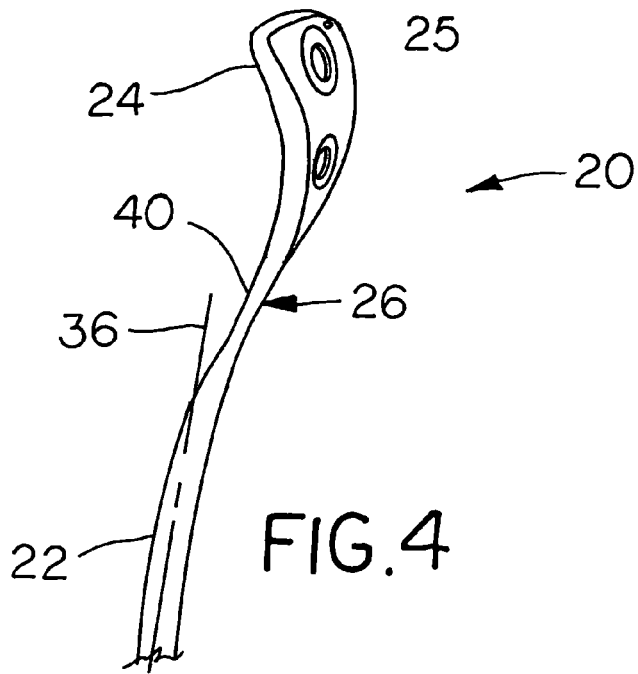
PRIOR ART
FIG 1
FIG. 2
FIG. 4

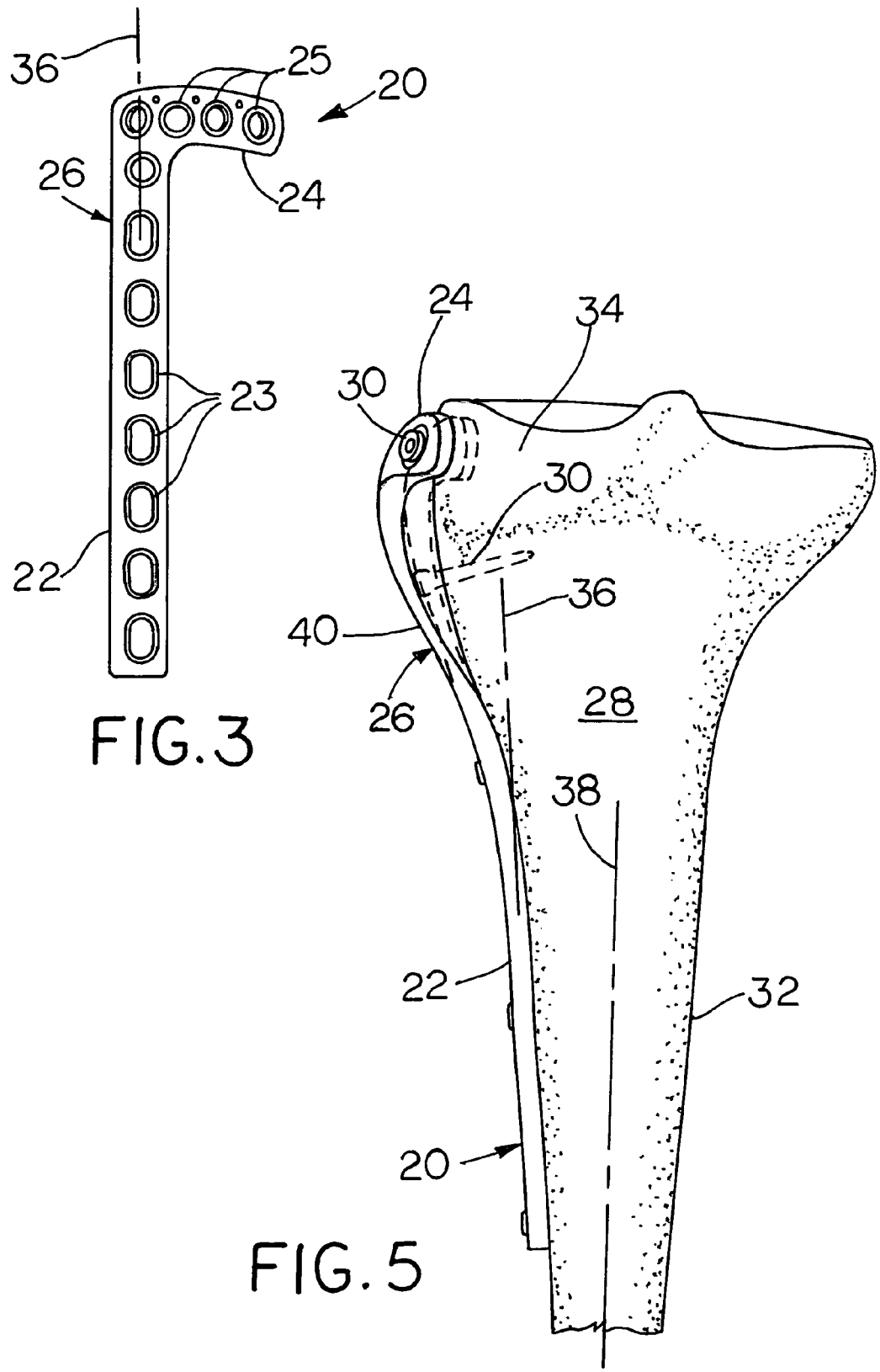

ORTHOPAEDIC BONE PLATE

CROSS-REFERENCE TO RELATED APPLICATIONS

This application is a Continuation of U.S. patent application Ser. No. 09/938,071 filed Aug. 23, 2001, which is a Continuation of U.S. patent application Ser. No. 09/309,368 filed May 11, 1999 (now U.S. Pat. No. 6,355,042), which is a Continuation of U.S. patent application Ser. No. 09/052,539 filed on Mar. 31, 1998 (now U.S. Pat. No. 5,938,664), the disclosures of which are hereby explicitly incorporated by reference herein.

BACKGROUND OF THE INVENTION

1. Field of the Invention

The present invention relates to orthopaedic bone plates, and, more particularly, to orthopaedic bone plates attached to an end and shaft of a bone.

2. Description of the related art

A bone plate is typically used to maintain different parts of a fractured or otherwise severed bone substantially stationary relative to each other during and/or after the healing process in which the bone mends together. Bones of the limbs include a shaft with a head at either end thereof. The head of a bone has a periphery which is either slightly or greatly enlarged relative to the periphery of the shaft to provide a larger load bearing surface at the end of the bone. Fractures of a bone in the region of the head may be particularly troublesome because of moving and/or soft tissues in the region of the bone joint.

It is known to provide a bone plate which attaches to both a head and the shaft of the bone to thereby maintain the head substantially stationary relative to the shaft. Such a bone plate includes an elongate portion which attaches to the shaft of the bone and a flared portion which attaches to the head of the bone using a plurality of bone screws. The elongate portion and the flared portion are both relatively thick in a direction transverse to the anatomical axis of the bone shaft such that the head and shaft of the bone do not move relative to each other after the bone plate is attached to the bone.

With a conventional bone plate as described above, the flared portion may be curved to accommodate the enlarged curvature of the head. It is quite common for the curvature of the flared portion to not exactly correspond to the curvature of the bone head. Rather, the bone plate has a shape corresponding to a shape of an average bone based upon statistical data. The relatively thick bone plate thus in essence provides a buttress roadmap for the surgeon to reconstruct the bone or place fragments of the bone against the bone plate during the reconstruction.

It is common practice with a thick bone plate as described above for an orthopaedic surgeon to place such a bone plate against the bone, observe the differences in curvature between the bone plate and bone, remove the bone plate and hammer or otherwise bend the bone plate to better fit the bone, and again place the bone plate against the bone. This process is repeated until a satisfactory fit is achieved between the bone plate and the bone.

What is needed in the art is a bone plate which more easily conforms to the shape of a bone without manually and permanently deflecting the bone plate with repeated fitting steps by trial and error.

SUMMARY OF THE INVENTION

The present invention provides an orthopaedic bone plate with a flared portion which can deflect toward and thereby conform to the shape of a bone when the elongate portion and flared portion are screwed to the bone. When attached to the bone, the bone plate also acts as a buttress surface with an improved anatomical approximation for smaller bone fragments.

The invention comprises, in one form thereof, an orthopaedic bone plate coupled to a bone having an enlarged head at one end thereof which is attached to a shaft. The bone plate includes an elongate portion, a flared portion and an intermediate portion. The elongate portion is attachable to the bone shaft using a plurality of bone screws. The elongate portion generally defines a longitudinal axis. The flared portion is attachable to the bone head using at least one bone screw. The intermediate portion interconnects the elongate portion and the flared portion. The intermediate portion is structured and arranged to allow the elongate portion and the flared portion to move relative to each other in a direction transverse to the longitudinal axis when the elongate portion and the flared portion are attached to the bone.

An advantage of the present invention is that the bone plate conforms to the shape of the bone by simply screwing the elongate portion and flared portion of the bone plate to the bone.

Another advantage is that the bone plate need not be manually bent or otherwise permanently deformed prior to being attached to the bone.

Yet another advantage is that an improved anatomical approximation of the bone plate is achieved through deflection of the bone plate, thereby resulting in superior bone reduction at the fracture.

A further advantage is that the improved anatomical approximation results in an increased contact interface between the bone plate and bone, resulting in more loading on the bone and less loading on the bone plate with a reduced possibility of fatigue failure of the bone plate.

A still further advantage is that the superior reduction of the bone results in improved loading between the bone pieces at the fracture site, resulting in improved healing.

An additional advantage is that the improved anatomical approximation results in an improved alignment of the articular surface at the joint of the bone, thereby inhibiting premature wear of the bone.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a side, fragmentary view of a conventional bone plate;

FIG. 2 is a perspective, fragmentary view of an embodiment of a bone plate of the present invention attached to a bone;

FIG. 3 is a front view of the bone plate of FIG. 2;

FIG. 4 is a side, fragmentary view of the bone plate of FIGS. 2 and 3; and

FIG. 5 is a side view of the bone plate of FIGS. 2-4 illustrating deflection of the flared portion and intermediate portion toward the bone.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

Referring now to the drawings, and particularly to FIG. 1, there is shown a side, fragmentary view of a conventional bone plate 10 including an elongate portion 12 and a flared portion 14. It may be seen that the thickness of elongate portion 12 and flared portion 14 are both substantially the same in FIG. 1. Such a conventional bone plate has a thickness which does not allow the bone plate to deflect without hammering or using other tools. Of course, the bone plate cannot be deflected while on the patient while using such tools. The bone plate must therefore be fitted to the bone and thereafter removed to place a permanent bend therein.

Although bone plate 10 shown in FIG. 1 has a relative constant thickness between the elongate portion and the flared portion, the thickness may also slightly tapper from the elongate portion to the flared portion. In either event, the thickness of known bone plates is such that the bone plate will not deflect after being attached to the bone, but rather must be bent or otherwise permanently deflected prior to being attached to the bone.

Referring now to FIGS. 2-5, there is shown an embodiment of a bone plate 20 of the present invention. Bone plate 20 includes an elongate portion 22, a flared portion 24 and an intermediate portion 26. As shown in FIG. 2, bone plate 20 may be attached to a bone, such as the proximal end of a tibia 28, using a plurality of bone screws 30. Tibia 28 includes a shaft 32 and an enlarged head 34 at one end thereof. Shaft 32 defines an anatomical axis of tibia 28.

Elongate portion 22 includes screw holes 23 allowing attachment to bone shaft 32 using a plurality of bone screws 30. In the embodiment shown, three bone screws 30 are used to attach elongate portion 22 to shaft 32; however, a different number of bone screws may also be utilized. Elongate portion 22 generally defines a longitudinal axis 36 which is disposed generally parallel to anatomical axis 38 of tibia 28. Of course, it will be appreciated that longitudinal axis 36 and anatomical axis 38 are not likely perfectly parallel with each other.

Flared portion 24 includes screw holes 25 allowing attachment to head 34 of tibia 28 using at least one bone screw 30. In the embodiment shown, two bone screws 30 are used to attach flared portion 24 with head 34; however, a different number of bone screws 30 may be used.

Intermediate portion 26 interconnects elongate portion 22 with flared portion 24 of bone plate 20. Intermediate portion 26 is configured to allow elongate portion 22 and flared portion 24 to move relative to each other in a direction transverse to each of longitudinal axis 36 and anatomical axis 38 when elongate portion 22 and flared portion 24 are attached to tibia 28. More particularly, intermediate portion 26 is formed with a thin region 40 which allows intermediate portion 26 to deflect in a direction generally towards longitudinal axis 36 when elongate portion 22 and flared portion 24 are attached to tibia 28. That is, bone plate 20 is attached to tibia 28 using a plurality of bone screws 30, as indicated above. Each of bone screws 30 has a shear strength within the bone after being fully seated in the bone and against bone plate 20. Thin region 40 is configured such that bone plate 22 bends or deflects when bone screws 30 are seated against bone plate 20 and into tibia 28. The relative thinness of bone plate 20 in thin region 40 thus depends in part upon the shear strength between bone screws 30 and tibia 28.

It is of course also possible to configure the thinness of bone plate 20 in thin region 40 such that intermediate portion 26 moves toward head 34 when a predetermined loading is applied thereto which is less than and not related to the shear strength of bone screws 30 within tibia 28. Configuring bone plate 20 to deflect at such a lower loading value ensures that intermediate portion 26 and flared portion 24 move toward head 34, rather than head 34 moving toward flared portion 24 (which may not be desirable for purposes of bone alignment).

To further ensure that bone plate 20 properly conforms to tibia 28, each of elongate portion 22, flared portion 24 and intermediate portion 26 are provided with a curvature on the surface abutting tibia 28 which defines a compound curvature corresponding to the typical shape of tibia 28. The compound curvature is derived from statistical data for the shape of a particular bone to which bone plate 20 is applied. That is, the compound curvature of bone plate 20 shown in FIGS. 2-5 for placement against a tibia 28 is likely different from the compound curvature of a bone plate attached to a different type of bone.

Aside from being configured to deflect in intermediate portion 26 toward longitudinal axis 36, bone plate 20 may also be configured such that flared portion 24 independently deflects toward head 34 of tibia 28. Thus, although flared portion 24 is slightly thicker than intermediate portion 26, flared portion 24 may also independently deflect toward longitudinal axis 36 and anatomical axis 38.

During orthopaedic surgery, bone plate 20 is placed against tibia 28 such that elongate portion 22 lies against bone shaft 32 and flared portion 24 lies against head 34. Elongate portion 22 is attached to bone shaft 32 using a plurality of bone screws 30. Flared portion 24 is attached to bone head 34 using at least one bone screw 30. When elongate portion 22 and flared portion 24 are each attached to tibia 28, intermediate portion 26 and flared portion 24 deflect toward anatomical axis 38 of tibia 28, thereby allowing bone plate 20 to conform to the peripheral shape of tibia 28.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic bone plate attachable to a bone using a plurality of bone screws, the bone having a peripheral shape, said orthopaedic bone plate comprising:

an elongate portion attachable to a shaft of the bone using a plurality of the bone screws, said elongate portion generally defining a longitudinal axis;

a flared portion attachable to a head of the bone using at least one of the bone screws; and an intermediate portion interconnecting said elongate portion and said flared portion, said intermediate portion having a bone contacting surface and an opposing outer surface, said intermediate portion including means for allowing the bone plate to conform to the peripheral shape of the bone when said elongate portion and said flared portion are attached to the bone, wherein the conformation of the plate to the peripheral shape of the bone is solely in response to attachment of said elongate portion and said flared portion to the bone.

2. The orthopaedic bone plate of claim 1, wherein said flared portion includes a means for allowing said flared portion to permanently deflect in a direction transverse to the longitudinal axis when said elongate portion and said flared portion are attached to the bone.

3. The orthopaedic bone plate of claim 2, wherein said allowing means of said flared portion comprises a thickness of the flared portion in a direction transverse to said longitudinal axis of said elongate portion.

4. The orthopaedic bone plate of claim 2, wherein said transverse direction of said means for allowing said flared portion to permanently deflect is generally toward the longitudinal axis.

5. The orthopaedic bone plate of claim 1, wherein each of said elongate portion and said flared portion have a plurality of screw holes.

6. The orthopaedic bone plate of claim 1, wherein each of said elongate portion, said flared portion and said intermediate portion are respectively curved in at least one direction transverse to the longitudinal axis.

7. The orthopaedic bone plate of claim 6, wherein said elongate portion, said flared portion and said intermediate portion are respectively curved to define a compound curvature of the bone plate in transverse directions generally toward and away from the longitudinal axis.

8. The orthopaedic bone plate of claim 1, wherein said allowing means of said intermediate portion comprises a thickness of said intermediate portion between said bone contacting surface and said opposing outer surface in a direction transverse to said longitudinal axis of said elongate portion.

9. The orthopaedic bone plate of claim 8, wherein said thickness allows said intermediate portion to deflect in a direction generally toward the longitudinal axis when said elongate portion and said flared portion are attached to the bone.

10. The orthopaedic bone plate of claim 8, wherein said elongate portion, said flared portion and said intermediate portion each have a thickness in a direction transverse to the longitudinal axis, said thickness of said elongate portion being greater than said thicknesses of said flared portion and said intermediate portion.

11. The orthopaedic bone plate of claim 10, wherein said thickness of said flared portion is greater than said thickness of said intermediate portion.

12. An orthopaedic bone plate attachable to a bone using a plurality of bone screws, said orthopaedic bone plate having a bone contacting surface and an opposing outer surface, said orthopaedic bone plate comprising:
   an elongate portion attachable to a shaft of the bone using the plurality of bone screws, said elongate portion generally defining a longitudinal axis, said elongate portion having a thickness between the bone contacting surface and the opposing outer surface in a direction transverse to the longitudinal axis;
   a flared portion attachable to a head of the bone using at least one of the plurality of bone screws, said flared portion having a thickness between the bone contacting surface and the opposing outer surface in a direction transverse to the longitudinal axis; and
   an intermediate portion interconnecting said elongate portion and said flared portion, said intermediate portion having a thickness between the bone contacting surface and the opposing outer surface in a direction transverse to the longitudinal axis, said thickness of said intermediate portion being less than said thickness of said elongate portion and said thickness of said flared portion;
   said thickness of said intermediate portion allowing said elongate portion and said flared portion to move relative to each other to conform to a peripheral shape of the bone in a direction transverse to the longitudinal axis of said elongate portion when said elongate portion and said flared portion are attached to the bone, wherein the conformation of said elongate portion and said flared portion to the peripheral shape of the bone is solely in response to attachment of said elongate portion and said flared portion to the bone.

13. The orthopaedic bone plate of claim 12, wherein said intermediate portion thickness allows said intermediate portion to permanently deflect in a direction generally toward the longitudinal axis when said elongate portion and said flared portion are attached to the bone.

14. The orthopaedic bone plate of claim 12, wherein said flared portion is structured and arranged to allow said flared portion to permanently deflect in a direction transverse to the longitudinal axis when said elongate portion and said flared portion are attached to the bone.

15. The orthopaedic bone plate of claim 14, wherein said flared portion thickness allows said elongate portion and said flared portion to move relative to each other in the transverse direction when said elongate portion and said flared portion are attached to the bone.

16. The orthopaedic bone plate of claim 14, wherein said transverse direction is generally toward the longitudinal axis.

17. The orthopaedic bone plate of claim 12, wherein each of said elongate portion and said flared portion have a plurality of screw holes.

18. The orthopaedic bone plate of claim 12, wherein said thicknesses of said elongate portion is greater than said thicknesses of flared portion and said intermediate portion.

19. The orthopaedic bone plate of claim 12, wherein each of said elongate portion, said flared portion and said intermediate portion are respectively curved in at least one direction transverse to the longitudinal axis.

20. The orthopaedic bone plate of claim 19, wherein said elongate portion, said flared portion and said intermediate portion are respectively curved to define a compound curvature of the bone plate in transverse directions generally toward and away from the longitudinal axis.

* * * * *